(12) United States Patent
Addesso-Dodd

(10) Patent No.: US 7,103,930 B1
(45) Date of Patent: Sep. 12, 2006

(54) DEVICE FOR THE CALIBRATION AND STANDARDIZATION OF HIP ROTATION

(75) Inventor: Vicki Addesso-Dodd, Little Ferry, NJ (US)

(73) Assignee: The Trustees of Columbia University, New York, NY (US)

( * ) Notice: Subject to any disclaimer, the term of this patent is extended or adjusted under 35 U.S.C. 154(b) by 332 days.

(21) Appl. No.: 10/103,628

(22) Filed: Mar. 21, 2002

(51) Int. Cl.
*A61B 5/055* (2006.01)

(52) U.S. Cl. .................................. 5/601; 5/621; 5/624

(58) Field of Classification Search .................... 5/601, 5/621, 622–624; 602/23, 26; 600/415
See application file for complete search history.

(56) References Cited

U.S. PATENT DOCUMENTS

| | | | |
|---|---|---|---|
| 4,181,297 A * | 1/1980 | Nichols | 5/650 |
| 4,232,681 A * | 11/1980 | Tulaszewski | 378/208 |
| 4,504,050 A * | 3/1985 | Osborne | 5/637 |
| 4,979,519 A * | 12/1990 | Chavarria et al. | 128/857 |
| 5,040,546 A * | 8/1991 | Deluhery | 5/646 |
| 5,445,152 A * | 8/1995 | Bell et al. | 600/415 |
| 5,522,792 A | 6/1996 | Bassett et al. | |
| D376,428 S * | 12/1996 | Lipson et al. | D24/183 |
| 5,640,958 A * | 6/1997 | Bonutti | 600/415 |
| 5,810,006 A * | 9/1998 | Votruba et al. | 600/415 |
| 5,864,901 A * | 2/1999 | Blumel | 5/610 |
| 6,442,777 B1 * | 9/2002 | Pauli | 5/601 |
| 6,516,045 B1 * | 2/2003 | Shepherd et al. | 378/53 |
| 6,609,260 B1 * | 8/2003 | Hand et al. | 5/600 |

OTHER PUBLICATIONS

Effect of Femoral Rotation On Bone Mineral Density Measurements With Dual Eenrgy X-Ray Absorptiometry. Goh JC, Low SL, Bose K. Calcif Tissue Int Nov. 1995; 57(5);340-3.
Effects of a New Positioner on the Precision of Hip Bone Mineral Density Measurements D. Hans, F. Duboeuf, A.M. Schott, S. Horn, L.V. Avioli, M.K. Drezner, P.J. Meunier Journal of Bone and Mineral Research, vol. 12, Nov. 12, 1997.
Bilateral Measurement of Femoral Bone Mineral Density R. Mazess, R.H. Nord, J.A. Hanson, H.S. Barden Journal of Clinical Densitiometry, vol. 3, No. 2. pp. 133-140, Summer 2000.

* cited by examiner

*Primary Examiner*—Patricia L. Engle
*Assistant Examiner*—Fredrick Conley
(74) *Attorney, Agent, or Firm*—Wolf, Block, Schorr & Solis-Cohen LLP; William H. Dippert

(57) ABSTRACT

The present invention concerns a device for the calibration and standardization of the rotation and movement of a patient's hip. More particularly the present invention relates to a device for the calibration and standardization of the rotation and movement of the hip for use in connection with improving the reproducibility and accuracy of a diagnostic procedure such as, for example, bone density measurement using dual x-ray absorptiometry (DXA).

14 Claims, 4 Drawing Sheets

DEVICE FOR THE CALIBRATION AND STANDARDIZATION OF HIP ROTATION

FIELD OF THE INVENTION

The present invention relates to a device for the standardization of the rotation and movement of the hip. More particularly the present invention relates to a device for the calibration and standardization of hip rotation during a diagnostic procedure. In a preferred use, the device of the invention improves the reproducibility and accuracy of bone density measurements using dual x-ray absorptiometry (DXA).

BACKGROUND OF THE INVENTION

Osteoporosis is a silent disease process that takes an enormous medical and economic tool on an aging population. This disease is characterized by low bone mass and microarchitectural deterioration of bone tissue, leading to bond fragility and an increase in the risk of fracture. Currently, osteoporosis affects an enormous number of people, and its prevalence will increase as the population ages. It is estimated that between 13% and 18% of postmenopausal Caucasian women in the United States, approximately 4 to 6 million, have osteoporosis, and an additional 30% to 50% (13 to 17 million) have low bone density at the hip. Based on data from the National health and Nutrition Examination Survey III (NHANES), the National Osteoporosis foundation has estimated that more than 10 million people in the United States have osteoporosis of the hip, and nearly 19 million more have low hip bone mass, placing them at increased risk for osteoporosis and fractures.

In addition to becoming a national health concern, osteoporotic fractures have created a heavy economic burden. In 1995, they were the presumed cause of 432,000 hospital admissions, almost 2.5 million physician visits and approximately 180,000 nursing home admissions in the United States that year. Direct medical expenditures alone for osteoporotic fractures in that year were estimated at $13.8 billion. These costs are anticipated to rise along with the growing elderly population. Hip fractures incur the greatest osteoporosis-related health care expenditures. by one estimate, the number of hip fractures and their associated costs could more than triple by the year 2040.

Fortunately, osteoporosis is preventable and treatable. Unfortunately, because there are no warning signs until fracture occurs, few people are currently being diagnosed in time to receive effective therapy during the disease's early phase. A Gallup survey commissioned by the NOF in 1991 found that three-fourths of all women aged 45 to 75, the group at highest risk, had never even discussed osteoporosis with their physician. There are many risk factors associated with the pathogenesis of osteoporotic fractures, including, but certainly not limited to, age, menopausal status, medications, and nutrition. In general, if one or more risk factors are present, a bone mineral density (BMD) test is appropriate.

Since its commercial inception in 1987, dual X-ray absorptiometry (DXA) has become the most widespread method for assessing a person's bone mineral status. M. Jergas et al., *Spinal and Femoral DXA for the Assessment of Spinal Osteoporisis*, Calcified Tissue International; Springer Verlag, New York, 1997, 61:351–357. Bone densitometry focuses on the bone mineral area density (BMD in g/cm2) of the proximal femur and spine in anterior-posterior projections. H. Franck et al., *Bone Mineral Density of Opposing Hips Using Dual Energy X-ray Absorptionmetry in Single-Beam and Fan-Beam Design*, Calcified Tissue International; Springer Verlag, New York, 1997, 61:445–447. However, because the hip has a relatively complex architecture, hip measurements are more demanding for the technician examining this site. Positioning of the hip is error-prone and the evaluation of serial scans may be affected by relatively small changes in rotation and abduction of the hip. Thus, the reproducibility of the hip BMD is generally poorer than that of the spinal BMD. M. Jergas et al., ibid. This poor reproducibility is both clinically and financially important, prevention of osteoporotic fractures, with the attendant reduction in health care costs, depends on early identification of individuals at risk for fracture. To detect these individuals earlier it is absolutely imperative that the accuracy of the BMD increases. In general, a practical clinical guideline is that a measured change in bone density should be equal to or greater than 2.8 times the precision error (coefficient of variation) of the measured technique in an individual patient to be considered "real" as compared to "artificial". Even with strict compliance to calibration and quality control procedures, the precision error of DXA measurements of the femoral neck is 2% to 3%, indicating that a change of at least 5.6% to 8.4% is needed to be considered real. L. F. Verheij et al., *Optimization of Follow-up Measurements of Bone Mass*. Journal of Nuclear Medicine; 1992, 33:1406–1410; C. Christiansen, *Postmenopausal Bone Loss and the Risk of Osteoporosis*, Osteoporosis International; 1994, 9(SI): S47–S51. However, strict compliance to calibration and quality control procedures is paramount to competent testing and therefore, one would expect much higher values clinically in less controlled environments.

Despite the obvious necessity for accuracy, few measures are currently taken to ensure reproducitility. Hologic, Inc., the United States leader in developing and manufacturing DXA systems, recognizes the importance and difficulty in achieving effective repositioning of the hip when performing serial scans. According to the company's QDR 4500 Operator's Manual, DXA machines are equipped with a "Hip Scan Positioning Fixture." In essence, this apparatus is simply a device to secure the foot following the manual rotation of the leg by the technician. According to the operator's manual, "the patient's foot should be placed in the hip scan positioning fixture. The fixture should then be aligned with the patient's leg, patient's leg rotated by turning the leg and foot, and the foot then placed against the positioning fixture. The strap is adjusted to snugly hold the foot, on the side to be examined, in the correct position." While this method provides adequate separation between the ischium and the femoral neck for the analysis of the scan, it should be obvious that it does little to enhance the reproducibility of serial scans. Unfortunately, this method does not provide any means of standardizing hip positioning and does not remove the operator-introduced error associated with repositioning.

In a variation of the aforementioned technology, Lunar Corporation published results for a dual-femur leg positioner and associated software. R. G. Mazess et al., *Bilateral Measurement of Femoral Bone Mineral Density*, J. Clin Den 2000; 3(2): 133–140. The research reported that the use of a dual-femur leg positioner and software allowed the simultaneous bilateral measurement of femoral bone mineral density and thus helped eliminate the error associated with the repositioning needed during single femur scans. However, the device has not eliminated the inherent flaws associated with the similar Hologic "Hip Scan Positioning Fixture", especially as it pertains to scans taken over several years, which are often most critical to the diagnosis and prevention of low bone mass diseases.

In another application to enhance reproducibility of hip positioning, U.S. Pat. No. 5,522,792, discloses an apparatus for maintaining an immobilized position for DXA scans. This invention immobilizes a patient's legs in a fully-extended, abducted position, while holding the patient's feet in adducted position. The present invention allows a patient to be immobilized by providing a frame on which a patient is placed, a centering member, a pair of knee restraints to secure the knees in a fully-extended and abducted position, and a pair of foot restraints to secure the patient's feet in an adducted position. While it is acknowledged that this device may help reduce the variation in hip positioning, there are several issues, which may limit the use of the device clinically. First, the hip positioning system, or HPS, provides only one single rotation angle because of the rigid nature of the design. Although this was able to optimize the projected length of the femoral neck, due to anatomical variation, no single rotation angle will result in optimal projection for all patients. Second, it has been found that subjects of short stature cannot be properly evaluated using the HPS. D. Hans et al., *Effects of a New Positioner on the Precision of Hip Bone Mineral Density Measurements*, J. Bone Miner Res 1997; 12(8): 1289–1294.

A report in *Calcified Tissue International*, 1995, describes a custom-designed positioning jig intended to minimize rotation of the hips during a BMD scan. An ankle foot orthosis (AFO) attached to the jig encased the foot and ankle while straps around the mid-thigh were intended to minimize any movement. The feet were placed 30 cm apart and the legs were internally rotated at 15° angles. This apparatus also presents several possible problems. First, according to Hologic and Lunar, the primary manufacturers of DXA equipment, proper femoral orientation is achieved with a rotation of 25°, 10° more than the angle recommended for optimal reproducibility when using the ankle foot orthosis and attached jig. And second, the jig initiates rotation at the foot or ankle; however, there is no means to assure that any rotation at the angle will correspond directly to a proportional change in angle at the hip. Many medical and physiological instances are foreseeable in which rotation of the ankle would product either little, or exaggerated movements, of the hip, dependent upon the condition.

One contrivance, which has attempted to address this issue, is the Norland "Advanced Hip Positioning Aid." Unlike many of the existing technologies, the Norland device attempts to rotate the femur by rotating the mid-thigh, rather than by rotating the feet. In vivo results indicate a significant improvement in precision using the new hip positional aid. However, the device still lacks features and considerations, which would promote its use in the clinical environment.

None of the foregoing prior art references provide a device which is simple to use, which would promote accurate, reproducible results regardless of the DXA machine used, and which could be used to measure either femur regardless of the characteristics of the patient to be evaluated.

Because the hip has a relatively complex architecture, hip measurements are more demanding for the technician examining this site. Positioning of the hip is error-prone, and the evaluation of serial scans may be affected by relatively small changes in rotation and abduction of the hip. Thus, the reproducibility of the hip BMD is generally poorer than that of the spinal BMD. Currently, few measures are taken to ensure reproducibility. One method is to strap the foot into a foot brace, the leg being rotated inwards and abducted from the midline. This provides adequate separation between the ischium and the femoral neck for the analysis of the scan but does not quantitate the degree of movement at the hip site. The second quality assurance measure involves having serial BMD's performed by the same technician on the same machine, however this has its obvious limitations and does not remove the human error.

OBJECTS OF THE INVENTION

It is an object of the present invention to provide a device which is capable of calibrating and standardizing hip rotation and/or movement.

It is also an object of the invention to provide a device for the calibration and standardization of hip rotation during a diagnostic procedure.

It is a further object of the present invention to provide a device which eliminates the error in the positioning of the hip site for use in a diagnostic procedure such as DXA analysis.

It is a yet further object of the present invention to provide a device which ensures reproducibility of the hip BMD that is operator independent.

These and other objects of the invention will become apparent from the following discussion of the invention.

SUMMARY OF THE INVENTION

The present invention provides for a device intended to standardize and calibrate the rotation and abduction of a patient's hip, especially the rotation and abduction that is necessary for a diagnostic procedure such as, for example, a BMD test. Preferably, the device will be capable of abducting and adducting the femur to various degrees as specified by a technician suitable for the nature of the scan and the patient's body type. In a preferred embodiment the device is used with DXA.

Different embodiments of the present invention are foreseen to accommodate different diagnostic models and to facilitate usage in the clinical environment. In a preferred embodiment of the invention, the patient's knee is secured in a flexible position on the device which is capable of pivoting and rotating at the discretion of the technician. The movement of the knee results in the subsequent rotation, adduction and abduction of the hip in a controlled and reproducible fashion. The device is capable of recording the movement of the knee either by a "ruler-like" method or, more preferably, by a digital display, thus allowing reproducibility of the positioning of the hip and knee and lessening the error involved in serial scans.

In another preferred embodiment, the present invention relates to a rotational device, which will be placed posterior (dorsal) to the patient's knee when the patient is in a supine position. The device will abduct the knee to a predetermined position, as judged suitable for the scan by the administering technician, and will be capable of locking in set position to allow a scan to be performed without risk or error. It is additionally preferred, although not necessary, that the device incorporate a method of restraining the knee during rotational movements to further reduce error. Although not wishing to be bound by theory, the device may rotate by any means, which provides both operator convenience and accuracy.

The construction and obvious advantages of the system provided for by the present invention will be more clearly

DETAILED DESCRIPTION OF THE INVENTION

Figure 1:
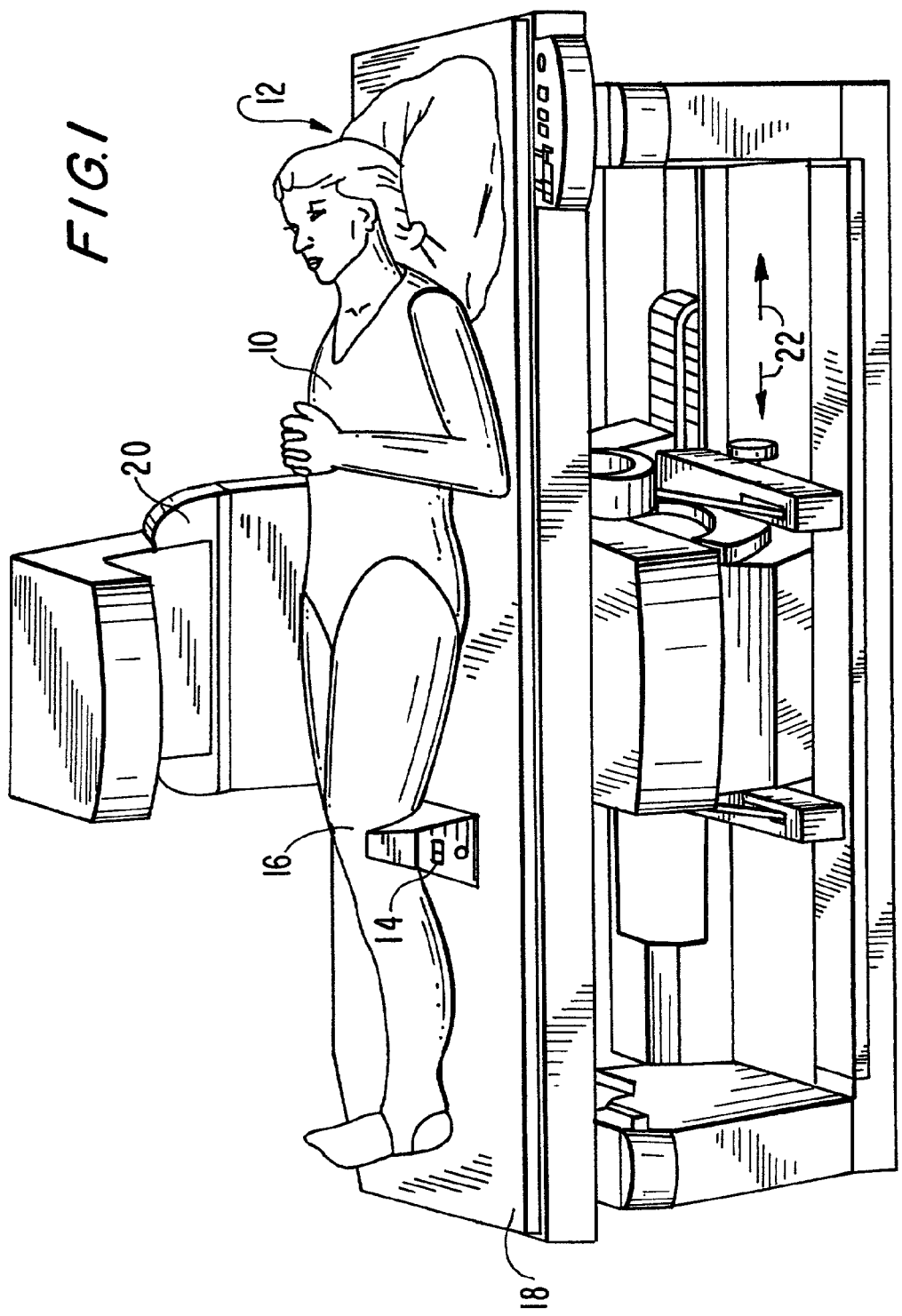
FIG. 1 is a perspective view of a patient lying on a typical DXA with the device of the invention in place secured about her left knee.

The present invention is directed to a device for the calibration and standardization of the rotation and movement of a patient's hip. It is within the scope of the invention that the device could be used for any medical, especially orthopedic, procedure. The present invention particularly relates to a device for the calibration and standardization of the rotation and movement of a patient's hip for use in connection with improving the reproducibility and accuracy of diagnostic procedures, such as bone density measurements using dual x-ray absorptiometry (DXA). It is within the scope of the invention that the device could be used with MRI or CATscan procedures as well.

The current invention provides a simple, effective, removable device to eliminate one of the major sources of variation involved in using diagnostic equipment and help lower the precision error ratio of such machines and measurements. The patient's knee is secured in a flexed position in the device of the invention, which is capable of pivoting and rotating the hip to a reproducible, controllable and measurable degree. The device can record the alignment of the knee mechanically or electronically, thus allowing reproducibility of the positioning of the hip and knee and lessening the error associated with the repositioning of the hip during scans of the femur in assessing a patient's bone mineral density and serial scans. The device can easily be installed, for example, on current DXA equipment or future models.

In a preferred used the device of the invention provides a simple method to increase the accuracy and reproducibility of DXA scans. Positioning of the hip is error-prone, and the evaluation of serial scans may be affected by relatively small changes in rotation and abduction of the hip, making the reproducibility of the hip BMD generally error prone. No other device offers an exact method with which to reproduce alignment. The current method used is to strap the foot into a foot brace, the leg being rotated inwards and abducted from the midline. This provides adequate separation between the ischium and the femoral neck for the analysis of the scan but suffers due to the lack of reproducibility of the placement of the knee and hip, thus decreasing the accuracy of the method and scan to determine risk of disease. The foot brace provides a reference point, not an exact measurement, and results in error when performing serial scans of the femur. The current invention will eliminate the error and will provide reproducibility that is operator-independent, thus eliminating a portion of the human error.

The device of the invention comprises a base portion which is generally flat on its bottom and has a generally curved or open upper portion for receiving a saddle portion. The saddle portion is configured such that is has an outer rigid curved surface which fits within the curved or open upper portion of the base. The outer edge of the rigid curved surface of the saddle is provided with a strip or ridge, which slidingly engages a mating groove located on the upper portion of the base such that when engaged the upper portion of the base is in intimate contact with the outer curved portion of said saddle with the strip of the saddle slidingly engaged within the groove of the base. The saddle portion is also provided with a handle on an outer side thereof to facilitate locating the saddle in the desired position along its path of travel within the base groove. Located on the outer surface of said saddle are a series of holes for positioning the saddle at the desired location along its path of travel. Also provided is a pin to insert into one of said holes in order to hold the saddle in the desired position.

The interior of said saddle portion is provided with a sufficient quantity and quality of firm foam rubber to secure a patient's knee in alignment and means to retain the said knee in the desired orientation relative to the saddle whilst the saddle is being rotated, thus also rotating the knee within the saddle and, as a consequence, the hip to which said knee is attached.

It is within the scope of the invention that two of the devices described could be used in a "side by side" manner, for example, for simultaneous scanning of dual hips.

The invention can perhaps be better appreciated from the drawings. FIG. 1 depicts a perspective view of a patient 10 lying on a typical DXA apparatus 12, where a positioning device 14 of the invention is secured about the patient's left knee 16. Positioning device 14 can be positioned along an upper surface 18 of DXA apparatus 12 in any position which corresponds to the location of the patient's knee 16 after patient 10 is properly positioned on DXA apparatus 12. Apparatus 12 comprises a scanner 20 that can be moved longitudinally in the direction of arrows 22.

Figure 2:
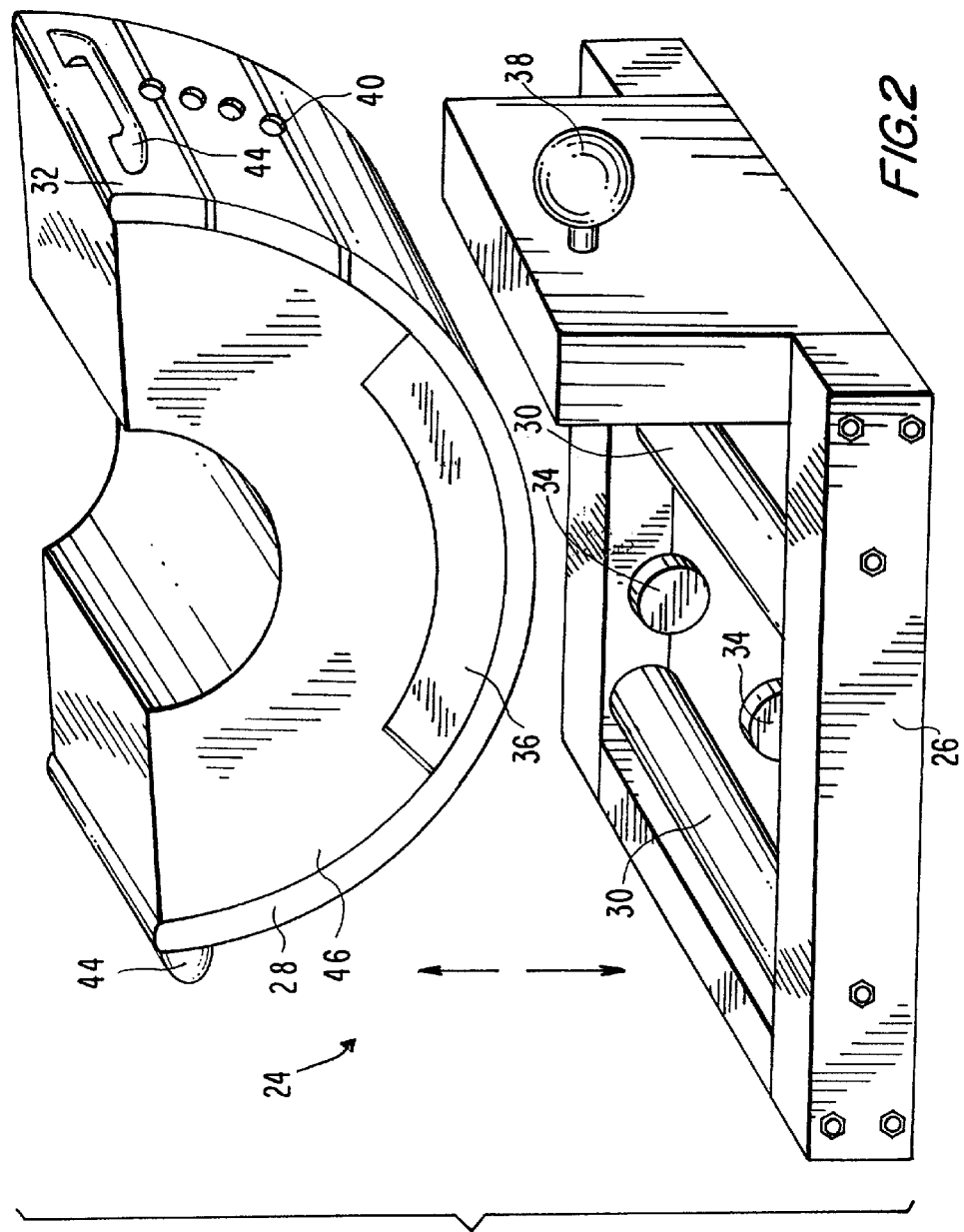
FIG. 2 is a perspective view of a preferred embodiment of the invention.
Figure 3:
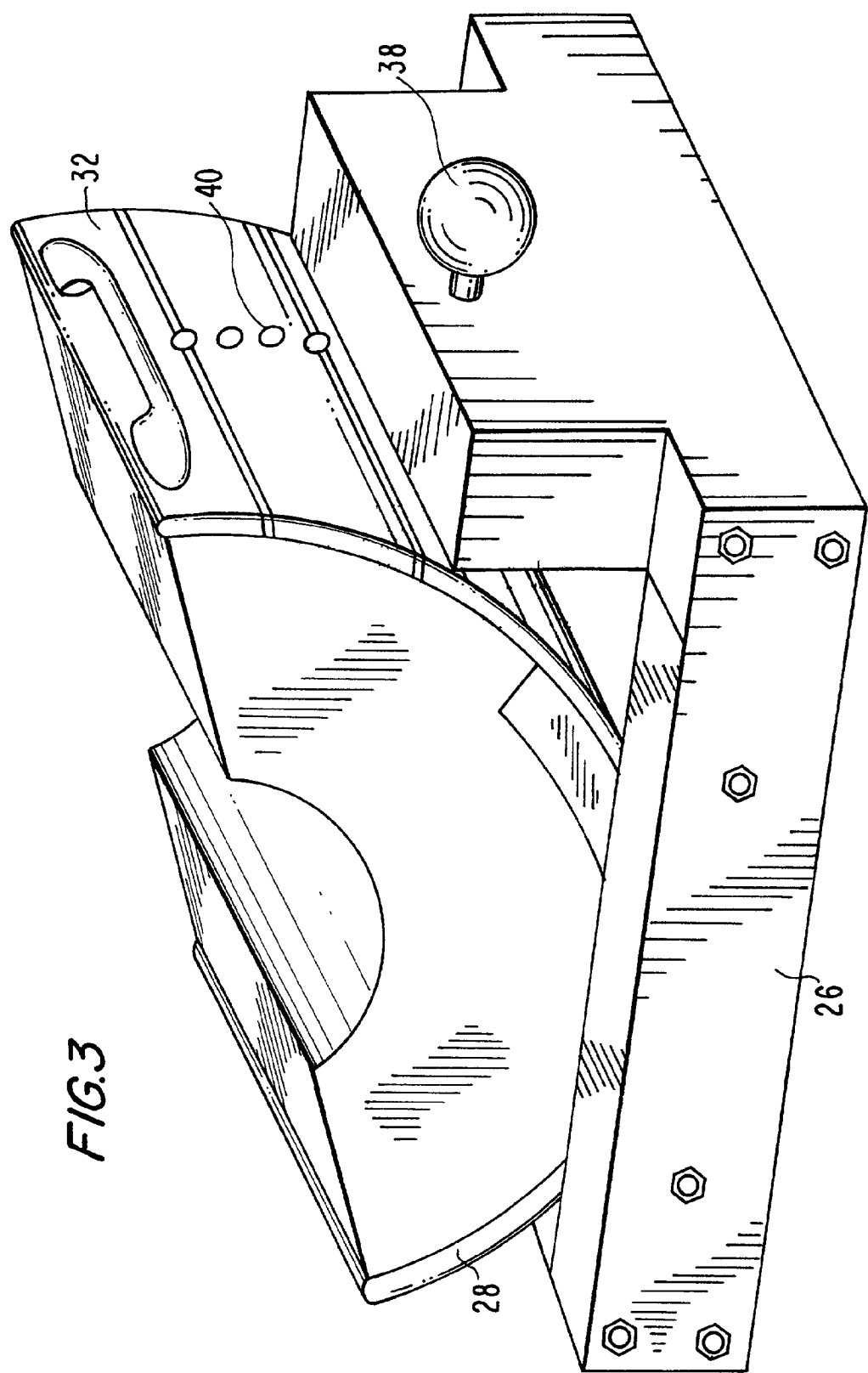
FIG. 3 is a perspective view of the preferred embodiment of the invention depicted in FIG. 2, showing the device in rotated position.

FIGS. 2 and 3 depict perspective views of a preferred embodiment of the invention with a positioning device 24 comprising a base portion 26 and a rotating or saddle portion 28. Base portion 26 comprises at least two rollers 30 that contact and support the outer surface 32 of saddle portion 46. Protrusions 34, which could be ball bearings or the like, engage oppositely positioned grooves 36 in saddle portion 28, to hold saddle rotating portion 28 in position relative to base portion 26 as saddle portion 28 rotates.

Base portion 26 comprises a preferably spring-constrained pin member 38, the inner portion of which (not shown) engages one of the holes 40 in outer surface 32. When pin member 38 is pulled away from saddle portion 28, saddle portion 28 can be rotated to a desired position. When the desired position is reached, pin member 38 is released and the inner portion of pin member 38 engages a hole 40 in outer surface 32. Handles 44 aid in positioning saddle portion 28.

Saddle portion 28 preferably has an inner layer 46 comprising a resiliently compressible material such as foam rubber or the like. Layer 46 most preferably should be removable and disposable, or it should have a covering that can be removed, disinfected, or sterilized.

Figure 4:
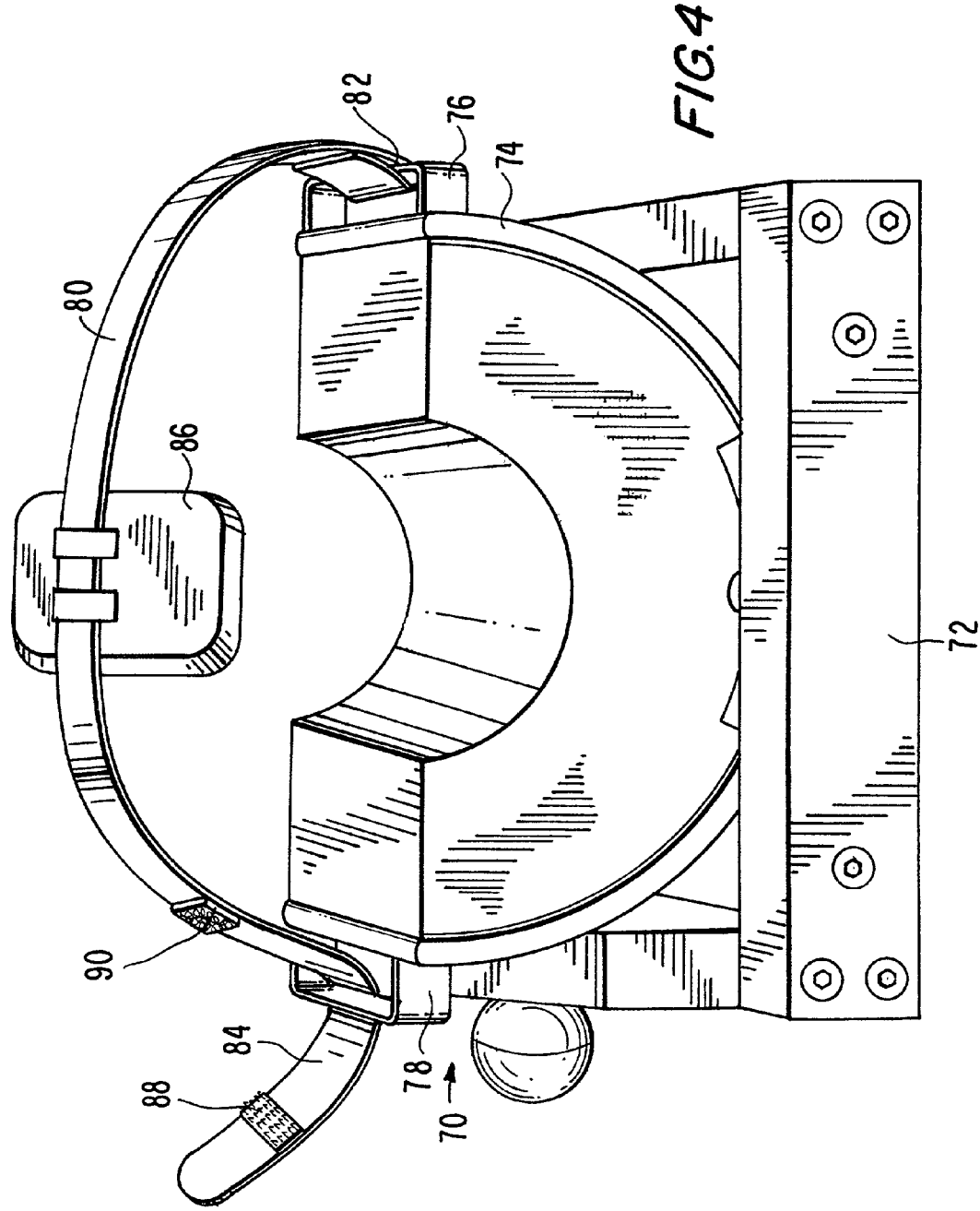
FIG. 4 is a perspective view of another embodiment of the invention.

According to the embodiment of the invention shown in FIG. 4, a device 70 of the invention has a base portion 72, a saddle portion 74, and handles 76, 78. A strap 80 is attached at its distal end 82 to handle 76, and a proximal end 84 of strap 80 is removably secured, for example, by velcro pads 88, 90, to handle 78. A cushion or padding 86 is adjustably attached to strap 80 to engage and/or protect a patient's knee (not shown).

The orientation of the saddle with relation to the base portion is indexed and precisely positioned via the holes and pin means shown in the preferred embodiment. Alternatively, in another preferred embodiment the rotation of the saddle portion with relation to the base portion is motorized and the positioning of the saddle with relation to the base portion is synchronized with a digital output which is displayed on a monitor for precise positioning and repositioning of the saddle.

It will be further apparent to one skilled in this art that the improvements provided for in the present invention, while described with relation to certain specific physical embodiments also lend themselves to being applied in other physical arrangements not specifically provided for herein, which are nonetheless within the spirit and scope of the invention taught here.

The invention claimed is:

1. An apparatus for the calibration and standardization of the rotation and movement of a patient's hip, said device comprising:
   a table having a horizontal upper surface for receiving a patient,
   a base member positioned on said table upper surface and having an open upper portion; and
   a saddle member having sides; an upper curved surface that is capable of engaging a knee of the patient; a lower rigid curved surface that rotates within the base member open upper portion to position the patient's knee; and opposing side surfaces between the upper and lower curved surfaces,
   wherein each side surface of the saddle member has an arcuate groove for slidingly engaging the open upper portion of the base member and the upper portion of the base member has protrusions for slidingly engaging the grooves of the saddle member.

2. The apparatus of claim 1, wherein the saddle member is provided with a handle on its lower rigid curved surface.

3. The apparatus of claim 1, wherein the saddle member is provided with a series of holes and a mating pin to retain the saddle member in a desired position.

4. The apparatus of claim 1, wherein the inner surface of the saddle member is provided with a firm foam retaining means for securing the patient's knee.

5. The apparatus of claim 1, wherein positioning of the saddle member is controlled manually.

6. The apparatus of claim 1, wherein positioning of the saddle member is controlled via a motor and the location of the saddle member with respect to the base is synchronized with a digital output which is displayed on a monitor.

7. The apparatus of claim 1 which also comprises means for performing a medical orthopedic or diagnostic procedure.

8. The apparatus of claim 7, wherein the means is capable of measuring bone density.

9. The apparatus of claim 8, wherein the means is capable of measuring bone density using dual x-ray absorptiometry.

10. The apparatus of claim 7, wherein the means is capable of performing an MRI or CAT scan.

11. In a medical procedure that concerns the calibration and standardization of the rotation and movement of a patient's hip to measure bone density using dual x-ray absorptiometry, the improvement wherein a knee of the patient is positioned in a device comprising a base member having an open upper portion and a saddle member having sides; an upper curved surface that is capable of engaging the knee of the patient; a lower rigid curved surface that rotates within the base member open upper portion to position said knee; and opposing side surfaces between the upper and lower curved surfaces,
   wherein each side surface of the saddle member has an arcuate groove for slidingly engaging the open upper portion of the base member and the upper portion of the base member has protrusions for slidingly engaging the grooves of the saddle member.

12. A device for the calibration and standardization of the rotation and movement of a patient's hip, said device comprising:
   a base member having a open upper portion; and
   a saddle member having sides; an upper curved surface that is capable of engaging a knee of the patient; a lower rigid curved surface that rotates within the base member open upper portion to position a knee of the patient; and opposing side surfaces between the upper and lower curved surfaces,
   wherein each side surface of the saddle member has an arcuate groove for slidingly engaging the open upper portion of the base member, the upper portion of the base member has protrusions for slidingly engaging the grooves of the saddle member, the saddle member is provided with a series of holes, and the base member has a mating pin for engaging the holes of the saddle member to retain the saddle member in a desired position.

13. A device for the calibration and standardization of the rotation and movement of a patient's hip, said device comprising:
   a base member having a open upper portion; and
   a saddle member having sides; an upper curved surface that is capable of engaging a knee of the patient; a lower rigid curved surface that rotates within the base member open upper portion to position a knee of the patient; and opposing side surfaces between the upper and lower curved surfaces,
   wherein each side surface of the saddle member has an arcuate groove for slidingly engaging the open upper portion of the base member; the upper portion of the base member has protrusions for slidingly engaging the grooves of the saddle member; and the inner surface of the saddle member is provided with a firm foam retaining means for securing the patient's knee.

14. A device for the calibration and standardization of the rotation and movement of a patient's hip, said device comprising:
   a base member having a open upper portion; and
   a saddle member having sides; an upper curved surface that is capable of engaging a knee of the patient; a lower rigid curved surface that rotates within the base member open upper portion to position a knee of the patient; and opposing side surfaces between the upper and lower curved surfaces,
   wherein the lower rigid curved surface each side surface of the saddle member has an arcuate groove for slidingly engaging the open upper portion of the base member; the upper portion of the base member has protrusions for slidingly engaging the grooves of the saddle member; and positioning of the saddle member is controlled manually.

* * * * *